(12) United States Patent
Varshney et al.

(10) Patent No.: US 9,600,793 B2
(45) Date of Patent: Mar. 21, 2017

(54) ACTIVE ODOR CANCELLATION

(71) Applicant: International Business Machines Corporation, Armonk, NY (US)

(72) Inventors: Kush R. Varshney, Yorktown Heights, NY (US); Lav R. Varshney, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 141 days.

(21) Appl. No.: 14/186,645

(22) Filed: Feb. 21, 2014

(65) Prior Publication Data

US 2015/0157752 A1    Jun. 11, 2015

Related U.S. Application Data

(60) Provisional application No. 61/913,703, filed on Dec. 9, 2013.

(51) Int. Cl.
*A61L 2/16* (2006.01)
*G06Q 10/06* (2012.01)
(Continued)

(52) U.S. Cl.
CPC ...... *G06Q 10/0637* (2013.01); *A23L 3/34095* (2013.01); *A61L 2/16* (2013.01); *G06F 17/3053* (2013.01); *G06F 17/30867* (2013.01); *G06F 17/30958* (2013.01); *G06F 17/50* (2013.01); *G06F 19/3475* (2013.01); *G06Q 10/063* (2013.01); *G06Q 10/1097* (2013.01); *G06Q 50/12* (2013.01); *A23V 2002/00* (2013.01);
(Continued)

(58) Field of Classification Search
CPC .................................................. G01N 33/0001
See application file for complete search history.

(56) References Cited

U.S. PATENT DOCUMENTS 5,303,846 A    4/1994  Shannon
5,783,544 A *  7/1998  Trinh ........................ A61L 9/14
                                                        252/8.61
(Continued)

FOREIGN PATENT DOCUMENTS

EP           1389047 B1      7/2009
IL    WO 2013035070 A1 *    3/2013    ......... G01N 33/0001
WO    WO 2013/035070 A1     3/2013

OTHER PUBLICATIONS

Puiu ("White Smell: the neutral fragrance discovered by scientists", ZME Science, Nov. 28, 2012). Obtained at http://www.zmescience.com/research/studies/white-smell-neutral-smell-discovered-04243/ on Jun. 7, 2016.*

(Continued)

*Primary Examiner* — Ling Choi
*Assistant Examiner* — Lanee Reuther
(74) *Attorney, Agent, or Firm* — Louis Percello

(57) ABSTRACT

The present disclosure relates to methods, devices and systems for calculating or selecting a first set of chemical compounds for an odor additive. For example, a method identifies a second set of chemical compounds present in a sample and intensities of individual chemical compounds in the second set of chemical compounds, and calculates the first set of chemical compounds for the odor additive such that an olfactory perception of a mixture of the sample and the odor additive is an olfactory white.

19 Claims, 5 Drawing Sheets

(51) Int. Cl.
  *A23L 3/3409* (2006.01)
  *G06Q 10/10* (2012.01)
  *G06Q 50/12* (2012.01)
  *G06F 17/50* (2006.01)
  *G06F 19/00* (2011.01)
  *G06F 17/30* (2006.01)
  *G09B 19/00* (2006.01)

(52) U.S. Cl.
  CPC ...... *B01D 2257/90* (2013.01); *G09B 19/0092* (2013.01)

(56) References Cited

U.S. PATENT DOCUMENTS

| | | | |
|---|---|---|---|
| 6,077,318 | A | 6/2000 | Trinh et al. |
| 6,248,135 | B1 | 6/2001 | Trinh et al. |
| 7,222,634 | B2 | 5/2007 | Hess et al. |
| 2002/0142477 | A1 | 10/2002 | Lewis et al. |
| 2005/0048186 | A1 | 3/2005 | Lehmberg et al. |
| 2007/0111251 | A1 | 5/2007 | Rosania et al. |
| 2009/0311403 | A1 | 12/2009 | Grab |
| 2010/0248390 | A1 | 9/2010 | Matsunami et al. |
| 2010/0265059 | A1 | 10/2010 | Melker et al. |
| 2011/0131047 | A1 | 6/2011 | Geiser et al. |
| 2015/0066386 | A1 | 3/2015 | Varshney |

OTHER PUBLICATIONS

International Search Report and Written Opinion of PCT/US2014/69108, dated Mar. 10, 2015, pp. 1-13.
G.M. Shephard, "Smell Images and the flavor system in the human brain," *Nature*, vol. 444, No. 7117, pp. 316-321, Nov. 2006.
Y.-Y. Ahn, S. E. Ahnert, J.P. Bagrow, and A.-L. Barabasi, "Flavor Network and the principles of food pairing," *Sci. Reports*, vol. 1, p. 196, Dec. 2011.
I. D. Fisk, A. Kettle, S. Hofmeister, A. Virdie, and J. S. Kenny, "Discrimination of Roast and Ground Coffee Aroma," *Flavour Journal*, vol. 1, No. 14, pp. 1-8, 2012.
T. Weiss, K. Snitz, A. Yablonka, R. M. Khan, D. Gafsou, E. Schneigman, N. Sobel, "Perceptual Convergence of multi-component mixtures in olfactory implies an olfactory white," *PNAS*, vol. 109, No. 49, Dec. 2012.
R. M. Khan, C.-H. Luk, A. Flinker, A. Aggarwal, H. Lapid, R. Haddad, N. Sobel, "Predicting Odor Pleasantness from Odorant Structure: Pleasantness as a Reflection of the Physical World," *The Journal of Neuroscience*, vol. 27, No. 37, Sep. 2007.
A. A. Koulakov, B. E. Kolterman, A. G. Enikolopov, D. Rinberg, "In Search of the Structure of Human Olfactory Space," *Frontiers in Neuroscience*, vol. 5, No. 65, pp. 1-8, Sep. 2011.
Young, J., "Making Sense of Scents," *Bowhunting World*, Apr. 25, 2011, http://www.grandviewoutdoors.com/articles/making-sense-of-scents#sthash.co69SuJg.dpbs.

\* cited by examiner

ACTIVE ODOR CANCELLATION

CROSS REFERENCE TO RELATED APPLICATIONS

This application claims priority to U.S. Provisional Patent Application Ser. No. 61/913,703, filed Dec. 9, 2013, which is herein incorporated by reference in its entirety.

FIELD OF THE DISCLOSURE

This disclosure relates generally to the field of indoor air quality and the perception of odor, and more specifically to altering the perception of odor using a selection of odor compounds.

BACKGROUND OF THE DISCLOSURE

Many people worldwide spend an overwhelming majority of their time indoors. For example, many people spend a significant portion of each day at work in an office. However, poor indoor air quality in buildings can decrease productivity in addition to causing visitors to experience dissatisfaction. The size of the effect on most aspects of office productivity is estimated to be 6-9%. Indoor air quality is important not only in buildings, but also in vehicles, in food storage areas, such as refrigerators, and so forth. To compensate for undesirable odors and poor air quality there are scent and odor products which roughly fall into four general product categories which include: masking, odor-adsorbing, odor-eliminating, and oxidizing. Masking involves covering one scent with another. Absorbing involves using active ingredients like baking soda, activated carbon, and the like. Eliminating involves using chemicals to react with odor molecules and turn the odor molecules into inert, odorless compounds. Oxidizing involves accelerating the breakdown of odor compounds. There are also many odor products available that claim to enhance emotional state and behavior.

SUMMARY OF THE DISCLOSURE

In one embodiment, the present disclosure is a method for calculating a first set of chemical compounds for an odor additive. For example, the method includes identifying a second set of chemical compounds present in a sample and intensities of individual chemical compounds in the second set of chemical compounds, and calculating the first set of chemical compounds for the odor additive such that an olfactory perception of a mixture of the sample and the odor additive is an olfactory white.

In another embodiment, the present disclosure is a device for calculating a first set of chemical compounds for an odor additive, where the device includes a processor and a computer-readable medium storing instructions, which when executed by the processor, cause the processor to perform operations. The operations include identifying a second set of chemical compounds present in a sample and intensities of individual chemical compounds in the second set of chemical compounds, and calculating the first set of chemical compounds for the odor additive such that an olfactory perception of a mixture of the sample and the odor additive is an olfactory white.

In another embodiment, the present disclosure is an additional method for selecting a first set of chemical compounds for an odor additive. The method includes identifying a second set of chemical compounds present in a sample, determining a set of physicochemical properties of chemical compounds present in the second set of chemical compounds and calculating physicochemical properties for the odor additive such that an olfactory perception of a mixture of the sample and the odor additive is an olfactory white. The method further includes selecting the first set of chemical compounds for the odor additive, where, when the first set of chemical compounds that are selected are mixed to form the odor additive, the odor additive comprises the physicochemical properties that are calculated for the odor additive.

In another embodiment, the present disclosure is a device that includes a database storing information identifying chemical compounds, physicochemical properties of the chemical compounds and perceptual properties of the chemical compounds, and a processor for receiving information regarding chemical compounds present in a sample and for calculating a set of chemical compounds for an odor additive based upon the information in the database such that an olfactory perception of a mixture of the sample and the odor additive is an olfactory white.

In still another embodiment, the present disclosure is a system for calculating a first set of chemical compounds for an odor additive system that includes a gas chromatography apparatus, a processor and a compound mixer. The gas chromatography apparatus is for identifying a second set of chemical compounds present in a sample. The processor is for calculating the first set of chemical compounds for the odor additive such that an olfactory perception of a mixture of the sample and the odor additive is an olfactory white. The compound mixer is for mixing the first set of chemical compounds that are calculated for the odor additive to create the odor additive.

BRIEF DESCRIPTION OF THE DRAWINGS

The teachings of the present disclosure can be readily understood by considering the following detailed description in conjunction with the accompanying drawings, in which.

DETAILED DESCRIPTION

Figure 1:
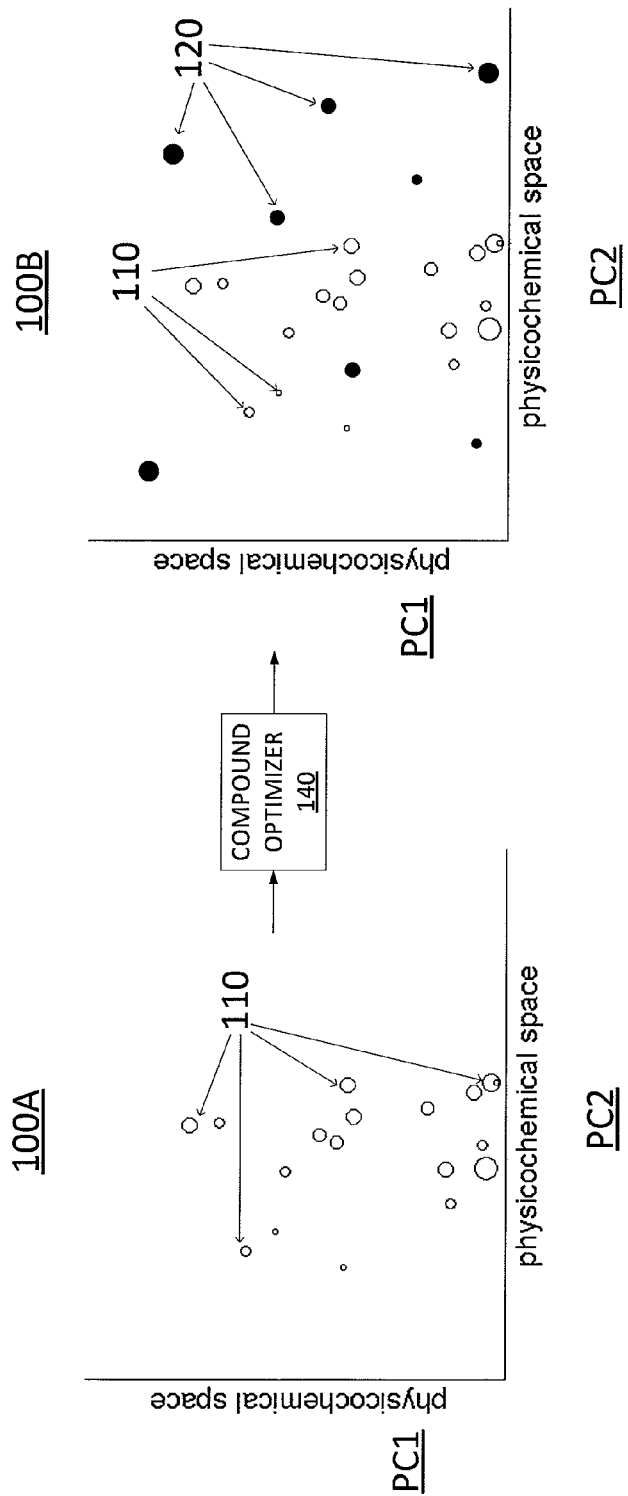
FIG. 1 illustrates two graphs of an olfactory/flavor physicochemical space reduced to two principal component dimensions, according to the present disclosure.

The present disclosure is directed to several problems relating to undesirable odors or tastes. For example, poor indoor air quality is known to reduce worker productivity in addition to simply being unpleasant to experience. As another example, human odors scare away game in hunting. Similarly, residual flavors/odors in the mouth may cause discomfort and may prevent enjoyment of subsequent foods and beverages. Further, residual odors from the mouth may be perceived as unpleasant odors by others nearby. In each case, malodors vary in space and time. For example, as a person walks through a building, he or she will encounter varying odors when travelling through different spaces. Similar variations in odor experience occur when driving, riding on a train, and so forth, as the vehicle passes through different environments. Likewise, residual flavors/odors of the mouth may change over time. For example, the perceived strength of the odor/flavor may diminish as more time passes since the last meal or last drink.

To address these and other issues, in one example the present disclosure provides an apparatus that senses odor compounds and quantities in the surrounding environment (e.g., in an indoor space, in an area around a hunter, etc.), calculates a mixture of odorant compounds that cancels the odor of the local environment to produce an olfactory white perception, and then produces the mixture (e.g., in the form of a spray or mist which can be applied to the environment). In another example, the present disclosure provides an apparatus that senses the residual flavor/odor in a person's mouth, calculates a mixture of flavor/odorant compounds that cancels the flavor to produce an olfactory white perception, and outputs a food, beverage, paste, gum, spray or sorbet containing the mixture.

Olfactory whiteness is a concept relating to olfactory perception that has analogs within other sensory fields. For example, in the area of visual perception, two mixtures, each containing an independent set of many different wavelengths, may produce a common color percept termed "white." In the realm of auditory perception, or "audition," two mixtures, each containing an independent set of many different frequencies, may produce "white noise." Visual and auditory whites emerge upon two conditions: when the mixture components span stimulus space, and when they are of equal intensity. Similarly, at least one study has shown that similar conditions apply to odorant mixtures which can be merged to produce an "olfactory white". For example, Weiss, et al. in "Perceptual convergence of multi-component mixtures in olfaction implies an olfactory white," Proceedings of the National Academy of Sciences of the United States of America, vol. 109, no. 49, pp. 19959-19964, Dec. 4, 2012, shows experimentally that mixtures of approximately 30 or more olfactory components which have features that span the stimulus space and which are of relatively equal intensity lead to a common olfactory perception, which has been termed olfactory white. Notably, mixtures of entirely different components that do not overlap or only partially overlap nevertheless can lead to the same perception of olfactory white.

In addition since the smell of foods is the key contributor to flavor, an olfactory white implies that a flavor white also exists. However, the stimulus space for olfactory perception, and therefore for flavor perception, is far more complicated than the analogs for visual and auditory perception. For example, for visual and auditory perception, there are well defined ranges of frequencies/wavelengths and magnitudes of signals that can be perceived by humans. Thus, each of these modes of perception essentially comprise a single dimension (frequency/wavelength of light and frequency/wavelength of sound waves, respectively). On the other hand, there is not a singular aspect to the perception of smell (and flavor). Rather, olfactory perception and flavor perception includes a vast number of dimensions.

For example, the olfactory perceptual space may include a hyper/multidimensional space that may include up to 146 or more perceptual labels/descriptors (e.g., 146 dimensions) which may include the well known descriptors: fruity, floral, fragrant, soapy, sweet, sulfurous, yeasty, and so forth. Each one of these descriptors (dimensions) may have a different intensity weight for different mixtures and for different common isolated chemical compounds that may be found in the ambient environment and in foods and fragrances. Thus, in the perceptual space, each mixture or chemical compound may be represented as a vector in X dimensions, where X is a number of available perceptual descriptors, wherein each perceptual descriptor occupies a different dimension, and where a value of the vector in each dimension relates to a perceived intensity of the mixture or chemical compound with respect to that particular descriptor.

It should be noted that the present disclosure may in some instances describe olfactory perceptual and physicochemical spaces, and in other instances describe flavor perceptual and physicochemical spaces. However, insofar as smell is the primary contributor to flavor, the olfactory and flavor spaces may be considered interchangeably for purposes of the present disclosure. In addition, it is noted that more than 100 common chemical compounds in foods and fragrances have been quantified in the olfactory perceptual space, e.g., using human test subjects to rate and quantify perceptions of the isolated chemical compounds. In other words, at the very least, these compounds have known vector representations in the perceptual space. However, there is a vastly greater number, more than 1000 known compounds, commonly used for olfaction and flavor research and which are known to contribute to smell and/or flavor perception.

In addition, a mixture and/or chemical compound can be represented as a vector based upon one or more physicochemical or physical descriptors in a physicochemical space. For example, the physicochemical space may have more than 1500 dimensions relating to the molecular properties of different chemical compounds, of which approximately only 40-50 are considered statistically relevant to olfaction and/or flavor. These physicochemical properties include: the molecule's polarity, a number of bonds, a number of hydrogen atoms, a number of heavy atoms, presence and quantity of esters (e.g., monoesters, diesters, triesters, etc.), aldehydes and/or ketones, a length of ester sidechain, and so forth. Thus, each chemical compound can be represented as a vector in the physicochemical space based upon its molecular properties. For example, a compound with 7 bonds and 5 hydrogen atoms and that is a diester may comprise a vector of [7, 5, 2] in the dimensions of "number of bonds" and "number of hydrogen atoms" and "number of ester groups." It should be noted that the present disclosure considers that olfactory perception (and flavor perception) correlates to features of molecules, rather than the identities of the molecules.

In one example, the perceptual space may comprise up to 146 or more dimensions, while the physicochemical space may comprise more than 1500 dimensions (or between 40 and 50 dimensions if limited to those considered most relevant to olfaction). However, each of the physicochemical and perceptual spaces may be collapsed into hyper/multidimensional spaces with a smaller number of dimensions. For example, any one or more dimensions in the full perceptual space may be collapsed into a lesser number of "principal component" dimensions, each principal component dimension including from one to several of the original dimensions. For example, a multidimensional space may be collapsed into a two-dimensional space having a first dimension, principal component 1, and a second dimension, principal component 2. In addition, in principal component analysis (PCA), different dimensions are selected for aggregation with one another such that in the resulting space with a reduced number of dimensions, a maximum variability in the data set is captured given the available number of dimensions in the reduced-dimensional space. Note that the principal component dimensions are orthogonal to one another. Thus, the features represented by each of the principal component dimensions remain orthogonal to one another.

Vectors in a hyper-dimensional space can similarly be collapsed to a lesser-dimensional vector by collapsing each of its constituent components in each of the collapsed dimensions. As just one example, FIG. 1 illustrates an exemplary graph 100A of the physicochemical space reduced to two principal component dimensions (PC1 and PC2). For instance, the points 110 illustrated on the graph 100A may represent the principal component vectors of different chemical compounds responsible for the odor in an ambient environment, in an indoor space, such as an office, a bathroom, a refrigerator, etc., the odor emanating from an individual, and so forth. In another example, the points 110 illustrated on the graph 100A may represent the principal component vectors of different chemical compounds responsible for the residual flavor and/or odor in a person's mouth, e.g., after consuming a food, drink or meal. In one example, the physicochemical and/or the perceptual space is normed such that different dimensions, relating to different properties which are not necessarily of the same type, are scaled accordingly. Further aspects of the example of FIG. 1 are described in greater detail below.

With respect to the olfactory perceptual space, it has been shown that only two principal component dimensions capture greater than 50 percent of the variance of known chemicals in the original 146-dimensional space. With only approximately 10 dimensions, nearly 90 percent of the variation can be retained. Similarly, it has been shown that the first two principal component dimensions in the physicochemical space may account for more than 40 percent of the entire variance in the physicochemical space, while the first 10 principal component dimensions can account for 70 percent of the variation.

In addition to the above, the perceptual space is known to generally correspond to the physicochemical space. In other words, attributes in the perceptual space can be predicted from attributes in the physicochemical space, and vice versa. In particular, more than 100 common compounds have been quantified in the perceptual space. Further, since the molecular properties of these chemicals are also known, a generalized correspondence between particular physicochemical properties in the physicochemical space and perceptual descriptors and magnitudes the perceptual space has been derived from this rich set of data. For example, it has been shown that with a two-dimensional perceptual space and a two-dimensional physicochemical space created by principal component analysis (PCA), there is a strong correlation between a first principal component dimension in the perceptual space and a first principal component dimension in the physicochemical space and a similarly strong correlation between a second principal component dimension in the perceptual space and a second principal component dimension in the physicochemical space.

It should be noted that these exemplary principal component dimensions are not observable in the real world and cannot be experienced and perceived as such. However, to provide some frame of reference, the perceptual descriptors most strongly associated with the first principal component dimension in the perceptual space may include fragrant/sweet at the one extreme and putrid/rancid at the other extreme, while the second principal component dimension is associated with the descriptors of ether/gasoline at one extreme and smoky/woody at the other extreme. Similarly, in the two-dimensional physicochemical space, the first principal component dimension may be most strongly associated with hydrophobicity and polarity while the second principal component dimension may be strongly associated with a number of carbon atoms, among other physicochemical properties.

The foregoing example describes the correlation between the first two principal component dimensions in the perceptual space and the first two principal component dimensions in the physicochemical space. This is perhaps the most important and the most useful statistical correlation between the perceptual and physicochemical spaces. However, it should be noted that the use of further correlations based upon individual physicochemical properties may also be employed by embodiments of the present disclosure. For example, the length of side-chains of dipeptide esters has been correlated to the degree of sweetness. Thus, a mathematical correspondence between the ester side-chain length of a compound (e.g., a dimension in the physicochemical space) and the sweetness and/or fruitiness (e.g., a single dimension, or two dimensions in the perceptual space) may be inferred.

As further isolated chemical components are quantified in the perceptual space, more accurate correlations between other physicochemical properties (physicochemical dimensions) and other perceptual descriptors (perceptual dimensions) can be inferred. The same framework can be extended to derive correspondences between the physicochemical space and the perceptual space for various additional chemical compounds that share similar features with the more than 100 chemical compounds that have previously been quantified in the perceptual space. In any case, a vector representation of a chemical compound in the perceptual space is associated with an analogous vector representation of the compound in the physicochemical space whether explicitly (e.g., for the at least 100 chemical compounds that have been quantified experimentally in the perceptual space) or by inference as described above (e.g., using the essentially direct correlation between the two-dimensional perceptual space and the two-dimensional physicochemical space).

Figure 2:
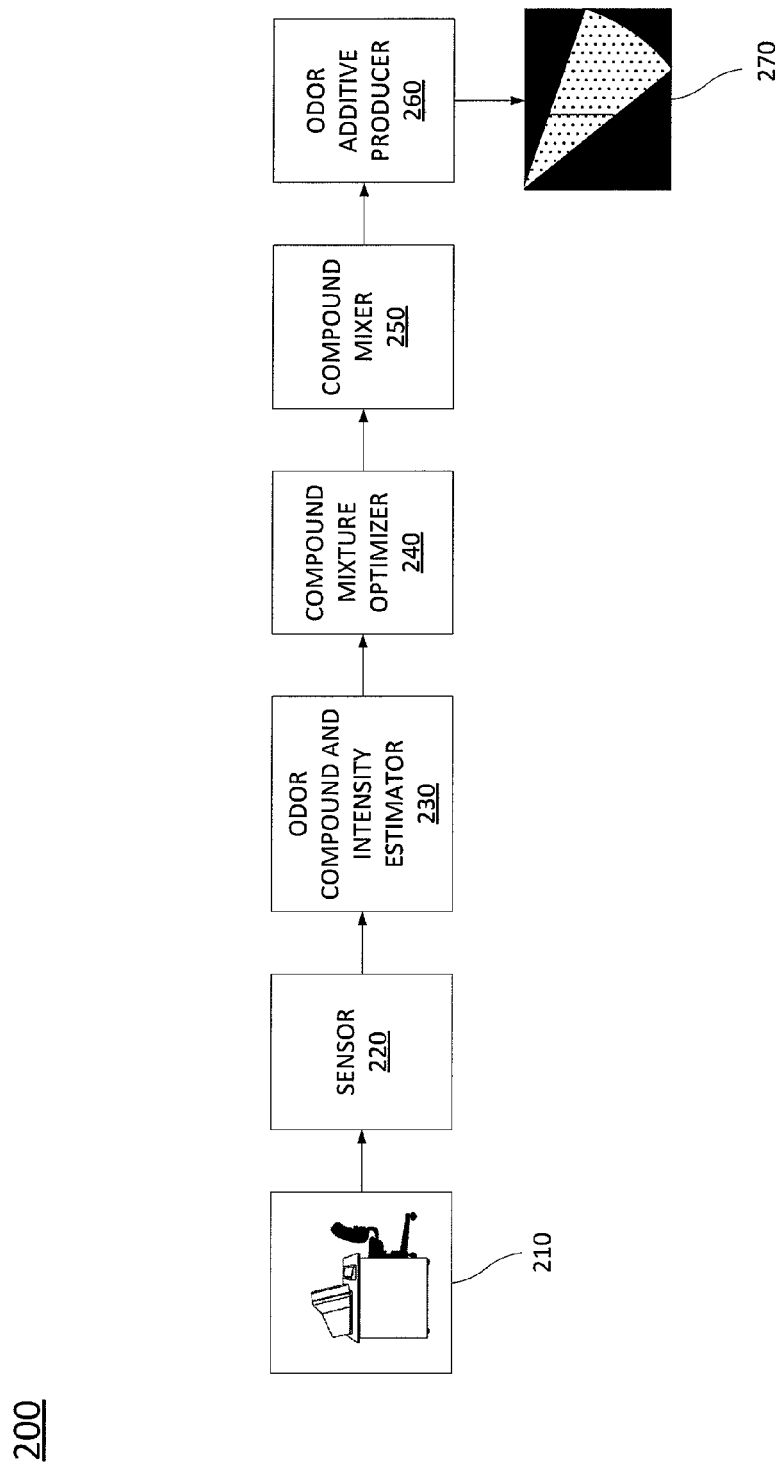
FIG. 2 is a high-level block diagram of an exemplary system for calculating and producing an odor additive, according to the present disclosure.

To further aid in understanding the present disclosure, FIG. 2 illustrates an exemplary system 200 for calculating a set of chemical compounds for an odor additive. In particular, the system 200 includes five main components: chemical sensor 220, odor compound and intensity estimator 230, compound mixture optimizer 240, compound mixer 250 and odor additive producer 260. The system 200 accepts as an input a sample from space 210 which is analyzed by chemical sensor 220.

In one embodiment, chemical sensor 220 is for detecting chemical components present in the sample. For example, if the sample is a sample of air from an office space, the chemical sensor 220 may detect numerous individual chemical components (also broadly referred to herein as "chemical compounds" or "odor compounds") in the air, along with the quantities and/or percentages by weight of each chemical component. In one embodiment, the chemical sensor 220 uses gas chromatography, which may include mass-spectrometry, photo-ionization detection, and the like, to determine the components that are present and their overall and/or relative quantities. Accordingly, chemical sensor 220 may comprise or may be part of a gas chromatography apparatus, as is known to those skilled in the art.

The next component of system 200 is the odor compound and intensity estimator 230, which determines the chemical compounds that are deemed to most strongly contribute to the olfactory perception of the sample. For instance, many of the chemical compounds detected by the chemical sensor 220 may only be present in trace amounts. In addition, many of the chemical compounds may be known to have little or no impact on olfactory perception, whereas others of the chemical compounds may be known to have a strong contribution to olfactory perception. Thus, the odor compound and intensity estimator 230 may obtain the data collected by the chemical sensor 220 and reduce the data set to include only the most important component chemicals, e.g., those with the greatest intensities, those know to contribute the most to olfactory perception, and so forth.

As also mentioned above, each chemical compound can be represented in the physicochemical space as a vector based directly upon known physical and/or chemical features of the chemical compound, e.g., number of bonds, number of carbon atoms, hydrophobicity, number of hydrogen atoms, length of ester sidechains, quantities of ester groups, alkyl groups and ketone groups, and so forth. As such, the odor compound and intensity estimator 230 may select the top X and/or Y chemical compounds of the sample and determine their physicochemical vectors. From these selected sets of vectors in the physicochemical space, the odor compound and intensity estimator 230 may then translate or project the selected set of vectors for the sample to respective vectors in the olfactory perceptual space. For example, in one embodiment the physicochemical properties of different compounds and corresponding perceptual descriptors may be stored in a database that is available to odor compound and intensity estimator 230.

Compound mixture optimizer 240 is tasked with calculating an optimal odor additive to be added to the environment from which the sample was obtained (e.g., the office space), such that an olfactory perception of the environment comprises an olfactory white. Accordingly, the compound mixture optimizer 240 performs such calculations over the olfactory perceptual space. However, this task may lead to an unbounded solution set (an essentially infinite number of solutions). As such, compound mixture optimizer 240 calculates at least one optimal solution to the problem. For instance, in one embodiment, the optimizer 240 may find a "lowest cost" or a low cost solution. In one embodiment, the lowest cost solution may be constrained by the availability or non-availability of certain compounds, the cost of such compounds, the relative health-related aspects of certain compounds, and so forth.

Once the optimal odor additive is calculated, compound mixer 250 may obtain and mix the desired quantities of the compounds that are calculated to produce the odor additive. In addition, odor additive producer 260 may further process the odor additive to place it in a form that is safe and suitable for human use and/or consumption. For example, the odor additive producer 260 may create a mist/spray 270. In another example the odor additive producer may create a candle, or any other type of liquid or solid mixture that produces a detectable odor.

It should be noted that in one example, the odor compound and intensity estimator 230 and compound mixture optimizer 240 may comprise a single device rather than separate devices or modules. As an example, the odor compound and intensity estimator 230 and compound mixture optimizer 240 may be embodied as a single computing device, such as general purpose computing device 500 of FIG. 5.

In one embodiment, the calculations made by compound mixture optimizer 240 may be implemented as follows:

$\mathfrak{R}_+^n$ represents a non-negative real space of chemical compound quantities. For example, n is the number of available chemical compounds, and number of dimensions (there are more than 1000 known and typically used for flavor/olfactory research).

h, a $\in \mathfrak{R}_+^n$ are odor compound vectors for the sample and the optimal compound mixture (i.e., the odor additive) respectively. For example, h is a vector comprising the chemical compounds and the amounts present in the sample and a is a vector comprised of a plurality of chemical compounds to be computed and their amounts.

P is a projection from $\mathfrak{R}_+^n$ to $\mathfrak{R}^d$ where d<n such that $\mathfrak{R}^d$ is a normed olfactory perceptual space of d dimensions. It should be noted that h and a can be mapped into the physicochemical space as respective sets of vectors in the physicochemical space, which may then be mapped into the perceptual space as respective vectors in the perceptual space.

w $\in \mathfrak{R}^d$ represents olfactory white (it is a vector in the perceptual space).

One way to represent the optimization problem for the compound mixture optimizer 240 is:

$$\min_a \|P(h+a) - w\| \qquad \text{(Equation 1)}$$

where P(h+a) is a vector in the perceptual space that corresponds to the set of vectors in the physicochemical space for a mixture of the sample and the odor additive.

It is noted that the minimization problem of Equation 1 has an unbounded solution set. Thus, the problem can be restated as:

$$\min_a \|P(h+a) - w\| + \lambda J(a) \qquad \text{(Equation 2)}$$

where $\lambda$ is a scalar and J(a) is a regularization term that is a function of vector a and which may incorporate objectives such as finding the solution with the minimum norm (including sparsity), minimum monetary cost, maximizing lifetime of compound mixer 250 by evenly using available constituent chemicals, minimizing the use of certain types of chemical compounds (e.g., minimizing the inclusion of alcohols, artificial ingredients and the like), minimizing the quantity or size of compounds to be added, designing for a desired spray/mist, liquid or solid form respectively, and other optimality principles.

It should be noted that in Equations 1 and 2, the problem attempts to find a vector a such that P(h+a) is as close to w as possible. In other words, select a set of compounds and select the amounts of each compound such that the perception of the environment with the existing chemical compounds/odor compounds and with the odor additive included is as close to olfactory white as possible. It should be noted that that flavor and smell are not subtractive. In other words, there are no flavors or smells which negate each other in the sense that some sound or light waves may cancel each other out to form a null or zero. Thus, olfactory white is not a true "zero" point, but has some positive perception.

It is also noted, however, that there is not a single olfactory white. Instead, many different combinations of approximately 30 or greater chemical compounds having features that span the stimulus space and which are of relatively equal intensity can be considered to be olfactory white. Accordingly, in one example the projection of these different olfactory/flavor white chemical compound combinations in the perceptual space may be set as: $W \subset \Re^d$. In this example, the optimization problem becomes:

$$\min_{a} \min_{w \in W} \|P(h+a) - w\| + \lambda J(a) \qquad \text{(Equation 3)}$$

where the goal is to find a vector, a, such that P(h+a) remains as close to w as possible, but where a range of different possible olfactory whites w∈W, may be used. For instance, any combination of approximately 30 or more chemical compounds having features that span the feature space and which have relatively equal intensities comprises an olfactory white. Thus, the compound mixture optimizer 240 may in one example use a w that results in a lowest cost solution for a via Equation 3.

Returning to the example of FIG. 1, the first graph 100A illustrates an example of the component vectors/points 110 of a sample in a reduced-dimension physicochemical space (e.g., having two principal component dimensions PC1 and PC2). As further illustrated in FIG. 1, the compound optimizer 140 may comprise a same or similar component to compound mixture optimizer 240 in FIG. 2. Thus, in the same manner as described with respect to compound mixture optimizer 240, compound optimizer 140 may calculate a set of chemical compounds to include in an odor additive such that the perception of the environment with the existing odor compounds and with the odor additive is as close to a perception of olfactory white as possible. Notably, the second graph 100B illustrates the points/vectors 120 in the physicochemical space representing the chemical components for the odor additive calculated by the compound optimizer 140 along with the points/vectors 110 for the sample.

Returning to the discussion of FIG. 2, in one embodiment a dynamic aspect may be incorporated in the system 200. For example, the chemical sensor 220 may continue to sample an environment and pass information regarding the detected chemical compounds and quantities to odor compound and intensity estimator 230. Odor compound and intensity estimator 230 selects components that most strongly contribute to odor/flavor on a continuous basis and passes the results to compound mixture optimizer 240. In turn, the compound mixture optimizer 240 may continuously calculate an optimal odor additive for the current time and/or projected time periods. For example, $\Re_+^{n+1}$ represents a non-negative real space of flavor compound quantities as above, but with an added dimension of time (hence the "n+1" number of dimensions). h(t), a(t) are odor compound vectors for the sample and the odor additive respectively as a function of time.

P is a projection from $\Re_+^{n+1}$ to $\Re_+^{d+1}$ where d<n such that $\Re_+^{d+1}$ is a normed flavor perceptual space of d+1 dimensions (where there is an added dimension of time). w∈W∈$\Re^{d+1}$ represents olfactory (and flavor) white (it is a vector in the perceptual space). Finally, λ is a scalar and J(a(t)) is a regularization term that is a function of vector a(t) and which may incorporate various objectives. The optimization problem then becomes solving for a(t) per the following:

$$\min_{a(t)} \min_{w \in W} \|P(h(t) + a(t)) - w\| + \lambda J(a(t)) \qquad \text{(Equation 4)}$$

In one embodiment the time component, t, represents a continuous time component. In another embodiment, t represents a discrete time component. In still another embodiment, t represents a planning horizon. For example, in an optimal system, t might comprise infinity (∞). However, projecting into the infinite future is not practical, nor can it be expected to be accurate. Nevertheless, the system 200 may operate out to some planning horizon and account for the "trajectory" of the environment from which the sample is taken. Notably, odors vary slowly in time. Thus, for instance, if the samples are taken from a vehicle that is passing through a noxious area, the noxious odor may gradually increase in intensity as the vehicle approaches the area, peak, and then diminish as the vehicle continues down the road. The odor may linger for some time in the vehicle even after travelling far from the noxious source due to the time it may take for the vehicle to fully replace the cabin air. However, based upon samples taken at least two different times, the compound mixture optimizer 240 may infer the physicochemical makeup of a future sample at a future time. Thus, the compound mixture optimizer 240 may continuously calculate an odor additive to be included in the environment from which the sample was taken.

In addition, with a statistical description of a(t), dynamic planning can be incorporated for the odor additive that is calculated. For example, some chemical components that may be included in the odor additive may be heavier than others and may fall to ground sooner, may be more volatile and dissipate into the environment sooner, and so forth. Thus, when projecting an odor additive to be introduced to the environment at a future time, t, compound mixture optimizer 240 may account for an anticipated continuing presence of chemical components that were included in the odor additive introduced to the environment at an earlier time period. In one example, λJ(a(t)) may maximize an availability of the first set of chemical compounds over the time period, minimize a cost of the first set of chemical compounds over the time period, and so forth. In other words, the system 200 considers the time-varying nature of an odor to continuously "cancel" the time-varying odor with a steady supply of odor additives.

Figure 3:
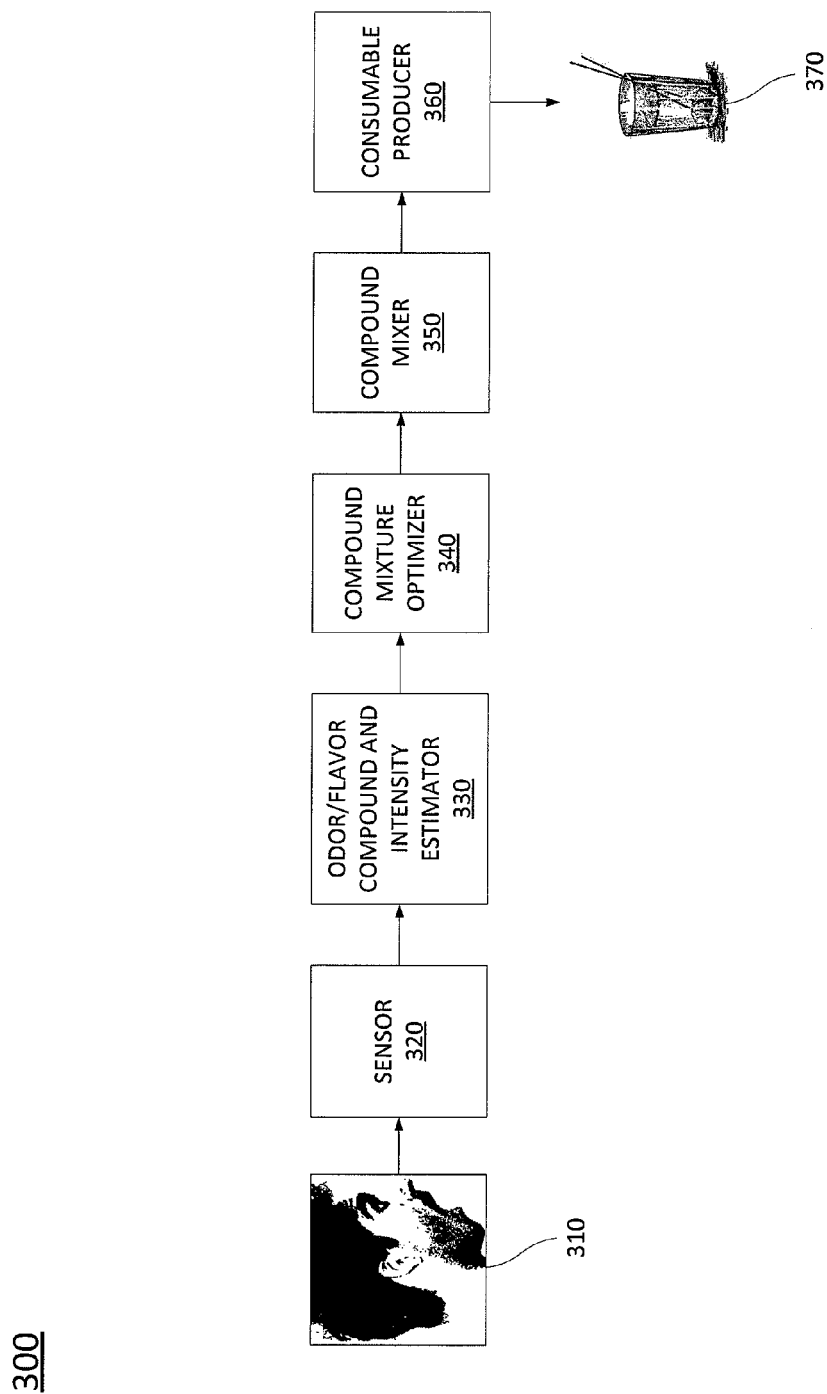
FIG. 3 is a high-level block diagram of an additional exemplary system for calculating and producing an odor additive, according to the present disclosure

To further aid in understanding the present disclosure, FIG. 3 illustrates an exemplary system 300 for calculating a set of chemical compounds for an odor/flavor additive. In particular, the system 300 includes five main components: chemical sensor 320, odor/flavor compound and intensity estimator 330, compound mixture optimizer 340, compound mixer 350 and additive producer 360. The system 300 accepts as an input a sample from in or around a person's mouth 310 which is analyzed by chemical sensor 320.

Notably, each of the components 320, 330, 340, 350 and 360 may perform the same or similar functions to components 220, 230, 240, 250 and 260 described above in connection with FIG. 2. However, the resulting output of the system 300 may instead comprise a consumable that is safe and fit for human consumption or for placing in a person's mouth, e.g., a food, beverage, paste, gum, spray, sorbet and the like.

In one embodiment, chemical sensor 320 may obtain a sample from a person's mouth 310. In one embodiment the chemical sensor 320 then uses gas chromatography, which may include mass-spectrometry, photo-ionization detection, and the like, to determine the components that are present in the sample and their overall and/or relative quantities. For instance, if the person has just recently eaten cheese, the chemical sensor 320 may detect more than 600 individual chemical components of cheese in the sample, along with the quantities and/or percentages by weight of each chemical component. In other words, the chemical components of cheese may dominate the odor of the sample and may also dominate the residual flavor/odor in the person's mouth.

The next component of system 300 is the odor/flavor compound and intensity estimator 330, which determines the chemical compounds that are deemed to most strongly contribute to the olfactory perception of the sample. For instance, the odor/flavor compound and intensity estimator 330 may obtain the data collected by the chemical sensor 320 and reduce the data set to include only the most important component chemicals, e.g., those with the greatest intensities, those know to contribute the most to olfactory perception, and so forth. For example, as mentioned above, a sample from a person's mouth who has just eaten cheese may include more than 600 different and unique chemical compounds that are detected. However, many of the 600 chemical compounds may only be present in trace amounts, especially when considering the residual presence of these chemical components in a sample from in or around a person's mouth. In addition, many of the 600 chemical compounds may be known to have little or no impact on flavor (and olfactory) perception, whereas other ones of the 600 chemical compounds may be known to have a strong contribution to the flavor (and olfactory) perception.

Compound mixture optimizer 340 is tasked with calculating an optimal odor additive to be added to the environment from which the sample was obtained (e.g., the person's mouth 310), such that an olfactory perception of the environment comprises an olfactory white. In other words, in one embodiment the goal is to produce a taste to the person that is perceived as olfactory white to replace the current residual flavor in the person's mouth. In another embodiment, the goal is such that the odor in and around the person's mouth 310 will be perceived by the person, and by any others nearby, as olfactory white. In one embodiment, both goals may be achieved by the odor/flavor additive calculated and generated by the system 300. In this regard, it should be noted that the present disclosure may in some instances refer to an odor additive and a flavor additive interchangeably. However, an odor additive in accordance with some embodiments may include chemical components which are safe to smell, but which are not safe to ingest. Thus, the number of safe odor additives that may be calculated and produced by the system 200 and/or the system 300 is potentially greater than the number of flavor additives.

In any case, the compound mixture optimizer 340 performs calculations over the olfactory perceptual space to determine an optimal odor additive. However, this task may lead to an unbounded solution set (an essentially infinite number of solutions). As such, compound mixture optimizer 340 calculates at least one optimal solution to the problem. For instance, in one embodiment, the compound mixture optimizer 340 may find a "lowest cost" or a low cost solution. In one embodiment, the lowest cost solution may be constrained by the availability or non-availability of certain compounds, the cost of such compounds, the relative health-related aspects of certain compounds (e.g., whether it is safe to ingest), and so forth. In one embodiment, the compound mixture optimizer 340 performs the same or similar calculations as described above in connection with the compound mixture optimizer 240 of FIG. 2.

Once the optimal odor additive is calculated, compound mixer 350 may obtain and mix the desired quantities of the compounds that are calculated to produce the odor additive. In addition, odor additive producer 360 may further process the odor additive to place it in a form that is safe and suitable for human use and/or consumption. For example, the odor additive producer 360 may create a consumable item 370, e.g., a food, beverage, paste, gum, spray, sorbet and the like that is fit for human consumption.

It should be noted that in one example, the odor/flavor compound and intensity estimator 330 and compound mixture optimizer 340 may comprise a single device rather than separate devices or modules. As an example, the odor compound and intensity estimator 330 and compound mixture optimizer 340 may be embodied as a single computing device, such as general purpose computing device 500 of FIG. 5.

Figure 4:
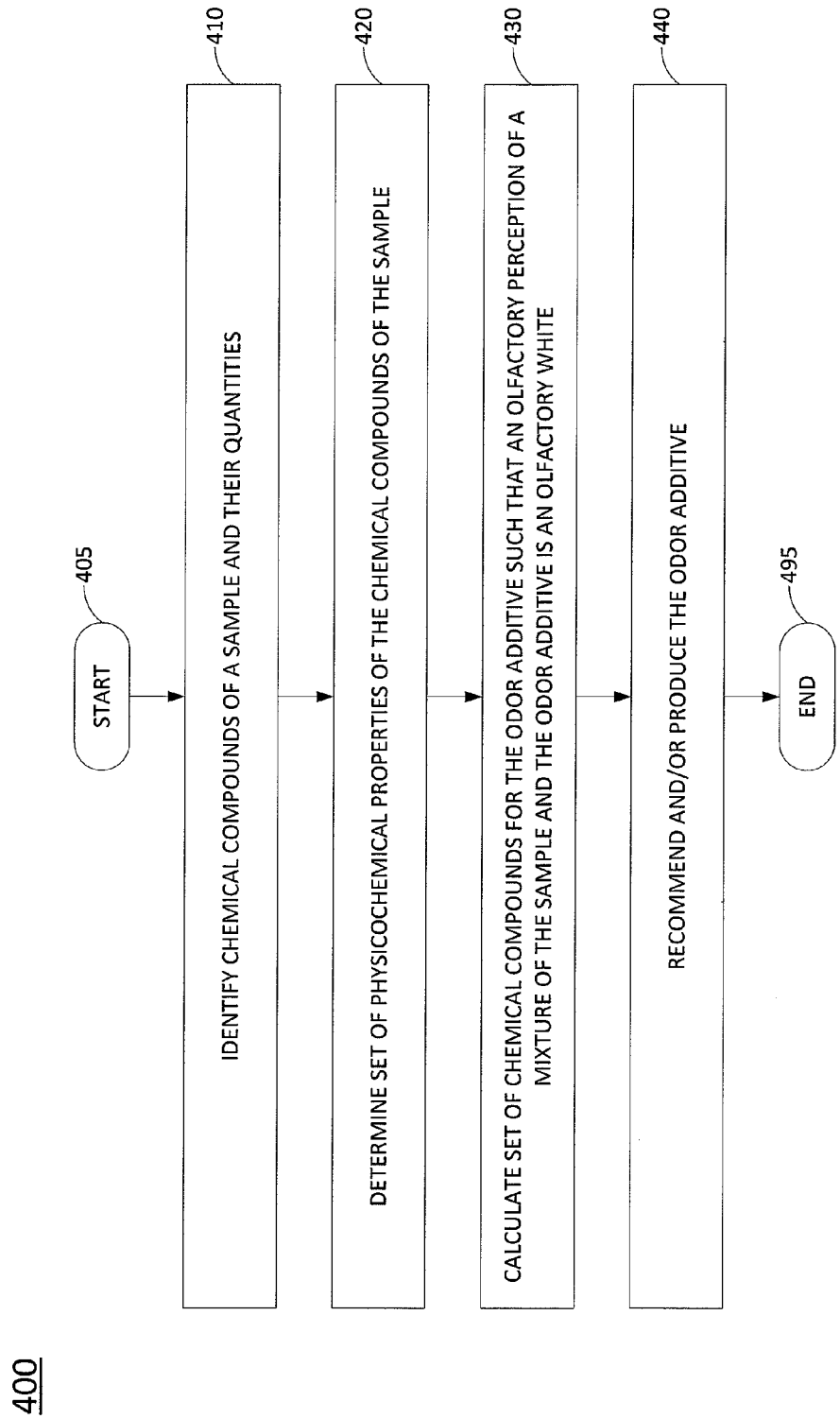
FIG. 4 is a flow diagram of an exemplary method for calculating or selecting a set of chemical compounds of an odor additive, according to the present disclosure.

FIG. 4 is a flow diagram illustrating one embodiment of a method 400 for calculating an odor additive. More specifically, the method 400 is for calculating and/or selecting a set of chemical compounds for an odor additive to be added to an odorous environment such that when the odor additive is introduced into the environment and is experienced in combination with the existing odor(s) of the environment, only the smell of olfactory white is perceived. It should be noted that in connection with FIG. 4, the discussion of "odors" may also be considered to include "flavors". Thus, in one example any one or more steps, functions and/or operations of the method 400 may be implemented by any one or more components of the system 200 in FIG. 2 or the system 300 in FIG. 3. Alternatively, or in addition, any one or more steps, functions and/or operations of the method 400 by may be performed by a computing device 500 and/or a processor of such a computing device as described in connection with FIG. 5 below. For illustrative purposes, the method 400 is described below in connection with this particular example.

The method 400 begins at step 405 and proceeds to step 410 where the processor identifies a set of chemical compounds of a sample and their quantities. For example, in one embodiment a gas chromatography apparatus may be used to sense the chemical compounds that constitute the sample and to determine the weights and/or relative amounts present in the sample. In one embodiment, the sample may comprise an air sample obtained from an indoor environment such as in an office, inside a refrigerator or other appliance, in a vehicle, and so forth. In another embodiment, the sample may be obtained from a space next to a person, an animal or other animate or inanimate odor source. In still another embodiment, the sample may comprise an air sample obtained from within or near the mouth of a person, an animal, etc. For example, gas chromatography may detect more than 600 unique chemical compounds that may contribute to residual flavor/odor in a person's mouth, e.g., where the person may have just finished eating cheese.

In step 420, the processor determines a set of physico-chemical properties of a plurality of chemical compounds of the sample. As an example, if the sample comprises cheese odors, a set of 600 or more chemical compounds may be detected. However, although the set of chemical compounds present may be relatively large, it is by and large known which compounds contribute to smell and flavor and which have little effect in the olfactory/flavor perceptual space. As such, certain compounds may be excluded from further analysis and processing at step 420, allowing the processor to focus on only the most important compounds. In addition, certain compounds may be present in such trace amounts that they may also be ignored and/or excluded from further processing at step 420, since these compounds also contribute little to the overall odor of the sample. Accordingly, step 420 may involve selecting only a portion of the chemical compounds present in the sample for further processing at step 430. Notably, in one embodiment the processor may obtain data regarding which compounds are strong contributors to odor and which are not from a database/data store, e.g., from any one or more of an attached memory, an external database accessed over a network, a disk drive, and the like. For instance, a database may be embodied in a storage device, such as storage device 506 in FIG. 5, discussed below.

In any case, once the chemical compounds of the sample are known, relevant physicochemical properties of each of the compounds may readily be determined. For example, there are more than 1000 well known chemical compounds that are used in olfactory and flavor research and which are known to contribute to smell and/or flavor. In addition, the physicochemical properties of these compounds are also well known such that, once a particular chemical compound is identified, it can be correlated to its physicochemical properties. For example, the identities of flavor compounds and their physicochemical properties may be stored in a list or database (e.g., the same database described above or a different database) such that the properties can simply be looked-up and indexed by chemical compound name/identity.

In one embodiment, at step 420 the processor may further create a vector in the physicochemical space for each of a plurality of chemical compounds selected for further processing. For instance, the processor may determine a vector for each compound in a multi-dimensional physicochemical space, where each dimension corresponds to a particular physicochemical property. Alternatively, or in addition, the processor may create a vector for each chemical compound in a lesser dimensional, "normed" space having principal component dimensions which may comprise linear projections of two or more dimensions aggregated with one another, wherein each principal component dimension is orthogonal to the other principal component dimensions, and where the principal component dimensions are selected to maintain a maximum variance in the data set given the resulting number of dimensions in the reduced-dimensional space. In any case, at step 420 the processor may create in the physicochemical space a set of vectors for the plurality of chemical compounds of the sample.

At step 430, the method 400 calculates a set of chemical compounds for the odor additive such that an olfactory perception of a mixture of the sample and the odor additive is an olfactory white. In other words, when the odor additive is introduced into the environment (which is assumed to be the same as the sample) and is experienced in combination with the existing odor(s) of the environment, only the smell (and/or taste) of olfactory white is perceived. For example, the processor may solve an optimization problem, e.g., based upon any one of Equations 1-4 above. For instance, the processor may determine a minimum cost vector comprising a plurality of chemical compounds and their relative quantities, using any of these equations. In one embodiment, the optimization problem involves finding a vector a such that P(h+a) is as close to w as possible, where w is a (vector) in the perceptual space representing the perception of an olfactory white and P(h+a) is a projection (vector) in the perceptual space representing the aggregate/combined perception of the sample, h, and the odor additive, a, combined together.

In one embodiment, vector a is calculated based upon a correlation between the perceptual space and the physicochemical space. In other words, desirable perceptual qualities and relative intensities that are necessary to bring P(h+a) into similarity with w are determined in the perceptual space, which are then capable of reverse-projection into desirable physicochemical properties in the physicochemical space. For example, with a two-dimensional perceptual space and a two-dimensional physicochemical space created by principal component analysis (PCA), there is a strong correlation between a first principal component dimension in the perceptual space and a first principal component dimension in the physicochemical space and a similarly strong correlation between a second principal component dimensions in the perceptual space and a second principal component dimension in the physicochemical space. Accordingly, at step 430 these and other known connections between perceptual descriptors and intensities and physicochemical properties may be used to reverse-project into the physicochemical space. In other words, desirable physicochemical properties (which may be represented by a vector in the physicochemical space) maybe identified by reverse-projecting from the perceptual space into the physicochemical space. In one embodiment, the processor may access the same database as discussed above or a different database which may store information regarding the connections between physicochemical properties and perceptual properties.

Accordingly, in one embodiment, at step 430, the processor calculates an odor additive comprising a set of chemical compounds such that when mixed together, the odor additive has these desirable physicochemical properties. It is noted that as stated, this task has practically an infinite number of solutions. For instance, as mentioned above a database may include a list of known chemical compounds and their physicochemical properties, such that chemical compounds that satisfy the criteria of the optimization problem can be determined by matching desirable physicochemical properties of the odor additive determined at step 430 with physicochemical properties of the different chemical compounds listed in the database. However, in the realm of available chemical compounds there exist numerous different individual chemical compounds which may satisfy one or more aspects of the particular physicochemical criteria determined at step 430. Thus, in one example, at step 430 the processor further calculates the food additive under certain constraints, such as minimizing the cost of the food additive based upon the costs of the different available chemical components or calculating the food additive components where certain chemical compounds may not be available or may be disfavored (e.g., alcohols, artificial versus naturally derived chemical components, and so forth). In one example, these optimization criteria/constraints are represented by the term $\lambda J(a)$ or $\lambda J(a(t))$ in Equations 2-4 above.

It is noted that olfactory white arises when approximately 30 or more chemical compounds are present and have features spanning the stimulus space with relatively equal intensity. Since olfactory white is a non-zero concept, the minimization of the distance between the projection of the combination of the sample and the odor additive mixed together and the vector of an olfactory white in the perceptual space results in the combination of the sample and the odor additive mixed together being perceived as the olfactory white.

It is also noted that there are many possible olfactory whites. Thus, in one embodiment step 430 involves finding a lowest cost solution using any available olfactory white (e.g., a lowest cost and/or closest-distance olfactory white). In other words, the particular lowest cost solution that is found at step 430 may be affected by external criteria, such as described above, e.g. $\lambda J(a)$ or $\lambda J(a(t))$, which may comprise a preference for naturally derived odor compounds, or less expensive or more readily available compounds, as well as by the distance to a closest olfactory white vector. This particular example is captured in Equations 3 and 4 above.

In addition, in one embodiment the method 400 may continuously calculate an optimal odor additive for the current time and/or for one or more projected time periods. For instance, implementation of the method 400 may follow Equation 4 above, with the steps of the method repeated to continuously and/or periodically calculate a set of chemical compounds for an optimal flavor additive at each time period. In such case, the method 400 may further involve forecasting the presence of odor compounds in the environment based at least two samples from previous time periods.

In one embodiment, at step 440 the processor further outputs a recommendation of the composition of the odor additive that is calculated and/or produces the odor additive based upon the set of chemical compounds that are determined/selected. For example, the processor may output a recommendation for an odor additive comprising a mixture of any number of different chemical compounds (e.g., 5-15 different compounds). It is noted that olfactory white arises when approximately 30 or more chemical compounds are present and have features spanning the stimulus space with relatively equal intensity. However, since the odor additive is being combined with the compounds that are already present in the sample (e.g., when it is introduced into the environment from which the sample was obtained), the necessary spanning of the stimulus space will often be achievable with an odor additive having substantially less than 30 chemical compounds. In one embodiment, the odor additive may be produced in the form of a spray or mist which can be applied to the environment. In another example, the odor additive may be produced in the form of a flavor additive that comprises a food, beverage, paste, gum, spray, sorbet and so forth containing the mixture.

Following step 440, the method 400 proceeds to step 495 where the method ends.

It should be noted that in various embodiments, any one or more of steps 410-440 of the method 400 may be performed in a different order that that which is illustrated herein. Similarly, any one or more of steps 410-440 may be considered to be optional steps, and may therefore be omitted without departing from the scope of the present disclosure. In addition, although not expressly specified above, one or more steps, functions or operations of method 400 may include a storing, displaying and/or outputting step as required for a particular application. In other words, any data, records, fields, and/or intermediate results discussed in the method can be stored, displayed and/or outputted to another device as required for a particular application. Furthermore, steps or blocks in FIG. 4 that recite a determining operation or involve a decision do not necessarily require that both branches of the determining operation be practiced. In other words, one of the branches of the determining operation can be deemed as an optional step.

Figure 5:
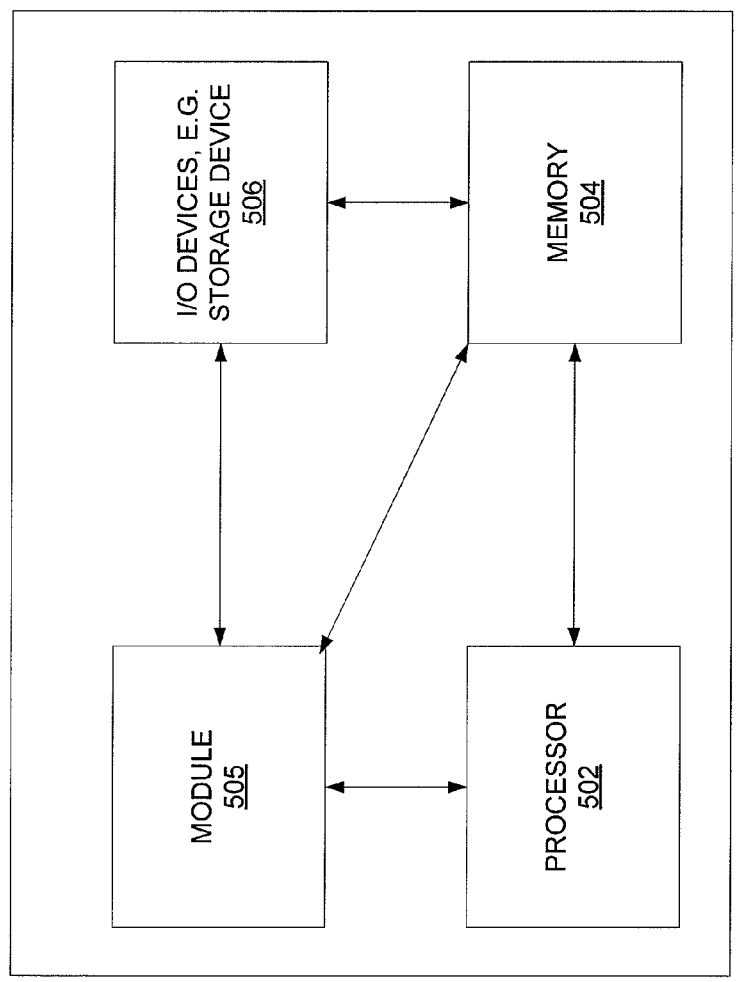
FIG. 5 is a high-level block diagram of a general purpose computing device suitable for use in performing the functions described herein.

FIG. 5 depicts a high-level block diagram of a general-purpose computer suitable for use in performing the functions described herein. As depicted in FIG. 5, the system 500 comprises a hardware processor element 502 (e.g., a central processing unit (CPU), a microprocessor, or a multi-core processor), a memory 504, e.g., random access memory (RAM) and/or read only memory (ROM), a module 505 for calculating or selecting a set of chemical compounds for an odor additive, and various input/output devices 506 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the general-purpose computer may employ a plurality of processor elements. Furthermore, although only one general-purpose computer is shown in the figure, if the method(s) as discussed above is implemented in a distributed manner for a particular illustrative example, i.e., the steps of the above method(s) or the entire method(s) are implemented across multiple general-purpose computers, then the general-purpose computer of this figure is intended to represent each of those multiple general-purpose computers.

It should be noted that the present disclosure can be implemented in software and/or in a combination of software and hardware, e.g., using application specific integrated circuits (ASIC), a general purpose computer or any other hardware equivalents, e.g., computer readable instructions pertaining to the respective systems and/or methods discussed above can be used to configure a hardware processor to perform the steps functions and/or operations of the above disclosed systems and methods. In one embodiment, instructions and data for the present module or process 505 for calculating or selecting a set of chemical compounds for an odor additive (e.g., a software program comprising computer-executable instructions) can be loaded into memory 504 and executed by hardware processor element 502 to implement the steps, functions or operations as discussed above in connection with the exemplary systems 200 and 300 and/or method 400. The processor executing the computer readable or software instructions relating to the above described method(s) can be perceived as a programmed processor or a specialized processor. As such, the present module 505 for calculating or selecting a set of chemical compounds for an odor additive (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server. In addition, it should be noted that the hardware processor can be configured or programmed to cause other devices to perform one or more operations as discussed above. In other words, the hardware processor may serve the function of a central controller directing other devices to perform the one or more operations as discussed above.

Referring to FIG. 5, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for formulating an odor additive, the method comprising:
    obtaining a sample from an ambient environment, the sample comprising a first set of chemical compounds that collectively induce a first non-white olfactory perception;
    identifying individual chemical compounds present in the first set of chemical compounds and respective intensities of the individual chemical compounds; and
    calculating a second set of chemical compounds that collectively induce a second olfactory perception different from the first non-white olfactory perception for the odor additive, such that a third olfactory perception induced when the odor additive is introduced to the ambient environment is an olfactory white, wherein the calculating the second set of chemical compounds comprises:
minimizing a difference between a vector projection of a mixture of the sample and the odor additive in a perceptual space with a vector projection of the olfactory white in the perceptual space.

2. The method of claim 1, further comprising:
producing the odor additive, wherein the odor additive comprises the second set of chemical compounds.

3. The method of claim 2, wherein the odor additive comprises a mist or a spray.

4. The method of claim 2, wherein the odor additive comprises a food, a beverage, a paste, a gum, a spray or a sorbet.

5. The method of claim 1, wherein the perceptual space comprises a multidimensional space where each dimension is associated with a different olfactory or flavor perceptual descriptor.

6. The method of claim 1, wherein the perceptual space comprises a multidimensional space where at least one dimension is associated with at least two different olfactory or flavor perceptual descriptors.

7. The method of claim 1, wherein the calculating the second set of chemical compounds comprises determining a set of physicochemical properties for the odor additive, where the determining the set of physicochemical properties for the odor additive is based upon at least one correlation between the perceptual space and a physicochemical space.

8. The method of claim 7, wherein the physicochemical space comprises a multidimensional space where each dimensions is associated with a different physicochemical property.

9. The method of claim 7, wherein the physicochemical space comprises a normed multidimensional space where at least one dimension is associated with at least two different physicochemical properties.

10. The method of claim 1, wherein the calculating the second set of chemical compounds comprises:
calculating a set of physicochemical properties for the odor additive such that a fourth olfactory perception of a mixture of the sample and the odor additive is the same as a fifth olfactory perception of only the olfactory white.

11. The method of claim 10, wherein the calculating the second set of chemical compounds further comprises:
selecting individual chemical compounds for inclusion in the second set of chemical compounds such that, when combined, the odor additive comprises the set of physicochemical properties.

12. The method of claim 1, wherein the first set of chemical compounds is identified by gas chromatography.

13. The method of claim 1, wherein the second set of chemical compounds is calculated based upon an availability of one or more chemical compounds in the second set of chemical compounds or such that a cost of the second set of chemical compounds is minimized.

14. The method of claim 1, further comprising:
determining a set of physicochemical properties of the first set of chemical compounds by performing a database lookup to match each of the individual chemical compounds with their respective physicochemical properties.

15. The method of claim 1, wherein the second set of chemical compounds is calculated over a time period, wherein the second set of chemical compounds that is calculated over the time period changes over the time period based upon a forecast of a third set of chemical compounds present in a future sample and intensities of individual chemical compounds in the third set of chemical compounds.

16. The method of claim 15, wherein the second set of chemical compounds and intensities of individual chemical compounds in the second set of chemical compounds over the time period are calculated to maximize an availability of the second set of chemical compounds over the time period or to minimize a cost of the second set of chemical compounds over the time period.

17. The method of claim 15, further comprising:
obtaining an additional sample from the ambient environment at a time during the time period that is different from a time during the time period at which the sample is obtained, wherein the additional sample comprises a fourth set of chemical compounds that collectively induce a third non-white olfactory perception, wherein the additional sample is obtained prior to the calculating;
identifying individual chemical compounds present in the fourth set of chemical compounds and respective intensities of the individual chemical compounds in the fourth set of chemical compounds, wherein the individual chemical compounds present in the fourth set of chemical compounds are identified prior to the calculating; and
forecasting the third set of chemical compounds present in the future sample and the intensities of the individual chemical compounds in the third set of chemical compounds based on analysis of the first set of chemical compounds and the fourth set of chemical compounds, wherein the forecasting is performed prior to the calculating.

18. The method of claim 1, wherein there is a partial overlap between the chemical compounds in the mixture of the sample and the odor additive and chemical compounds in the olfactory white.

19. The method of claim 1, wherein there is a partial overlap between components of the first set of chemical compounds and the second set of chemical compounds.

* * * * *